United States Patent [19]
Goldberg et al.

[11] Patent Number: 5,480,975
[45] Date of Patent: Jan. 2, 1996

[54] INDUCTION OF VASCULAR ENDOTHELIAL GROWTH FACTOR (VEGF) BY TRANSITION METALS

[75] Inventors: Mark A. Goldberg, Boston; Andrew P. Levy, Brookline, both of Mass.

[73] Assignee: Brigham and Women's Hospital, Boston, Mass.

[21] Appl. No.: 193,569

[22] Filed: Feb. 8, 1994

[51] Int. Cl.$^6$ .......... A61K 33/24; A61K 33/30; A61K 33/32; A61K 33/34

[52] U.S. Cl. .......... 530/399; 424/484; 424/617; 424/630; 424/639; 424/641; 424/642; 424/646; 424/655

[58] Field of Search .......... 514/964, 965, 514/969, 866, 925, 928, 2, 21, 42, 43; 530/399; 424/484, 617, 630, 639, 641, 642, 646, 655

[56] References Cited

U.S. PATENT DOCUMENTS 4,834,985  5/1989  Elger et al. .......... 424/488

OTHER PUBLICATIONS

Huheey, Inorganic Chemistry principles of structure and reactivity, second edition, Harper & Row Publishers, New York, N.Y., (1978), pp. 748–752.

Budavari, Editor, The Merck Index an encyclopedia of Chemicals, Drugs, and biologicals, eleventh edition, Published by Merck & Co., Inc., Rahway, N.J., (1989), pp. 1027–1028.

*Primary Examiner*—Ronald W. Griffin
*Attorney, Agent, or Firm*—Fish & Richardson

[57] ABSTRACT

Transition metal ions enhance the ability of the body to increase vascularization, particularly for revascularizing damaged tissues, apparently because they enhance expression of the vegF gene, so as to increase VEGF levels. According, hypoxic tissue damage can be treated or prophylactically reduced by administering a composition comprising a transition metal ion capable of stimulating vascularization. Treatment can be accomplished using compositions of matter which include a transition metal ion in a sterile, biologically compatible carrier, packaged as a unit dosage effective to increase vascularization in hypoxic tissue. For systemic administration, the transition metal ion is formulated at a concentration that is non-toxic and ineffective to increase vascularization in non-hypoxic tissue. For local administration, the transition metal ions are formulated in a slow-releasing carrier to release the transition metal ions continually over a prolonged period in an amount effective to increase vascularization locally. For example, for topical application, the composition may be a salve, a gel, or a patch. For internal slow release or for topical application, the composition may be formulated in a slow release matrix.

26 Claims, 1 Drawing Sheet

INDUCTION OF VASCULAR ENDOTHELIAL GROWTH FACTOR (VEGF) BY TRANSITION METALS

STATEMENT AS TO FEDERALLY SPONSORED RESEARCH

This invention was funded at least in part by a grant from the United States government (Grant No. RO1-DK- 45098), and the U.S. government has certain rights in the invention.

BACKGROUND OF THE INVENTION

This invention relates to methods and compositions for treatment or prophylaxis of tissue damage, particularly tissue damage incident to hypoxia.

Tissue damage can result when oxygen supply is insufficient to meet metabolic demands. This problem is clinically significant in that morbidity and mortality often result from tissue hypoxia, i.e., a drop in the partial pressure of oxygen to a given tissue below a level at which the cells are able to perform their normal functions aerobically. Under these conditions, the cells die or are forced to switch to alternate metabolism (e.g., glycolysis). Hypoxia can be caused by various medical conditions, including atherosclerosis, chronic illness, trauma, and even surgical procedures. Individuals affected include patients with atherosclerotic heart disease, peripheral vascular disease, cerebral vascular disease and those with problems of wound healing.

The physiological response to hypoxia has been studied at the level of organ systems and cells. Adaptive responses include increased respiratory rate, changes in vascular tone, the stimulation of red blood cell formation and new blood vessel formation (angiogenesis). These adaptations enhance cellular survival during periods of low oxygen availability. Less is known about the molecular mechanisms inducing the response, although the expression of certain genes is regulated following periods of hypoxic shock, including genes encoding: erythropoietin (Beru et al., 1986; Boundourant and Koury, 1986), platelet-derived growth factor B chain (Kourembanas et al., 1990), endothelin (Kourembanas et al., 1991), interleukin-1α (Shreeniwas et al., 1990) ornithine decarboxylase (Longo et al., 1993), and vascular endothelial growth factor (Shweiki et al., 1992; Plate et al., 1992). These genes may perform protective and recovery functions in the affected tissue.

The vascular endothelial growth factor gene (vegF), encoding the protein product known as VEGF or vascular permeability factor, is expressed in many tissue types. Various treatments using VEGF have been suggested (e.g., Criscuolo et al., 1989; U.S. Pat. Nos. 5,073,492, 5,194,596, 5,219,739), for ameliorating conditions such as myocardial infarction, diabetic ulcers, and surgical wounds.

SUMMARY OF THE INVENTION

Transition metal ions will enhance the ability of the body to increase vascularization, particularly for revascularizing damaged tissues. Without wishing to bind ourselves to a specific mechanism, it appears that certain transition metal ions enhance expression of the VEGF gene, so as to increase VEGF levels and thereby enhance vascularization.

Accordingly, one aspect of the invention generally features a method of treatment or prophylaxis of hypoxic tissue damage in a patient by administering a composition comprising a transition metal ion that is capable of stimulating vascularization and is present in an amount sufficient to do so.

In one preferred embodiment of the invention, the composition is administered locally to the hypoxic tissue. For example, the composition is administered topically as a salve or patch; alternatively, it is administered from a controlled, slow-release matrix.

In an alternative embodiment, the composition is systemically administered at a concentration that is non-toxic and ineffective to increase vascularization in non-toxic tissue.

In either embodiment, preferred transition metal ions are those capable of inducing expression of the vascular endothelial growth factor (VEGF) gene. Specific ions useful in the invention include: manganese, cobalt, or nickel. More than one transition metal ion may be administered simultaneously.

The invention can generally be used to treat individuals affected including patients with atherosclerotic heart disease, peripheral vascular disease, cerebral vascular disease and those with problems of wound healing. The invention is particularly useful for treatment or prophylaxis of hypoxic damage to cardiac tissue, e.g., in those presenting with angina due to atherosclerosis, or those presenting with transient ischemic attacks (TIA's). It is also useful for treating diabetic ulcers or healing traumatic or surgical wounds.

A second aspect of the invention features compositions of matter suitable for administration to a human patient, which include a transition metal ion in a sterile, biologically compatible carrier packaged as a unit dosage effective to increase vascularization in hypoxic tissue. "Biologically compatible" as used herein indicates that the medium contains only components that allow normal biological function at a level that is acceptable as an in vivo therapeutic. These compositions are suitable for administration to a human patient.

The preferred metal ions in the second aspect of the invention are those discussed above. For systemic administration, the transition metal ion is formulated to provide a concentration in the treated tissue of between 1 μM–300 μM. Most preferably, the ion concentration is non-toxic and ineffective to increase vascularization in non-hypoxic tissue, for example, for local administration, the transition metal ion is formulated in a slow-releasing carrier to release the transition metal ions continually over a prolonged period in an amount effective to increase vascularization locally. For example, the composition may be formulated to release the transition metal ion at a rate of between 1 μg and 10 mg/hour for at least one day (assuming treatment of a local volume of about 100 ml). For topical application, the composition may be a salve, a gel, or a patch. For internal slow release or for topical application, the composition may be formulated in a slow release matrix.

The invention utilizes the body's own response to injury, enhancing the protective properties invoked by hypoxic states; it can ameliorate hypoxic injury to areas at risk (e.g., stimulate collateral vessel formation in the myocardium); and the treatment can be applied to only the affected areas to avoid systemic effects.

Other features and advantages of the invention will be apparent from the following description of the preferred embodiments, the drawings and the claims.

BRIEF DESCRIPTION OF THE DRAWING

The file of this patent contains at least one photograph. Copies of this patent with photographs will be provided by the Patent and Trademark Office upon request and payment of the necessary fee.

DESCRIPTION OF THE PREFERRED EMBODIMENTS

Figure 1:
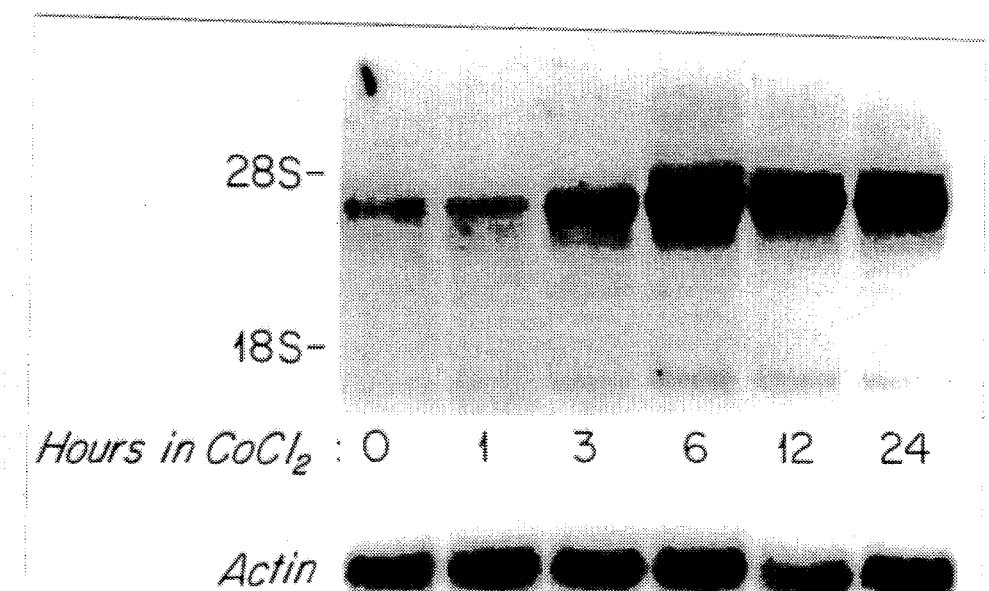
FIG. 1 shows induction of VEGF mRNA in the human hepatoma cell line Hep3B. RNA blot analysis of RNA from Hep3B cells grown for 0, 1, 3, 6, 12, or 24 hours in 100 μM $CoCl_2$. β-actin mRNA controls are depicted at the bottom of the figure.

We offer the following description of the selection of preferred transition metal ions, as well as preferred methods and indications for administering them so as to enhance the ability of the body to revascularize damaged tissues or increase vasculature (e.g., to prevent hypoxic damage) in accordance with our discovery.

I. Selection of transition metal ions

The transition metals are the group consisting of the fourth, fifth and sixth levels of the periodic table, those which fill the d orbital. They include such elements as Ni, Co, Mn, Zn, V, Cr, Fe, Cu, Mo, etc. The preferred candidate metal ions for use are manganese, cobalt and nickel, the most preferred metal ion being manganese.

Selection of other appropriate metal ions involves determining whether, and at what level, the ion will induce VEGF expression. Particularly for systemic applications, selection also involves a review of toxicity. Suitable techniques for those determinations are provided below in Example 1. Preferred ions are those with a substantial range between VEGF induction and toxicity.

II. Compositions and formulations of transition metal ions

This method is suitable for treatment of both internal or superficial hypoxic damage, treatment methods being either internal administration of the transition metal (systemic or local) in the form of a salt or free ion in a biologically compatible tablet or capsule, gel, or liquid; or external application in the form of a biologically compatible powder, salve, liquid, or transdermal patch. Any physiologically acceptable anion such as chloride, sulfate, etc., can be included in the composition.

A particularly preferred method of application is as a salve or transdermal patch that can be directly applied to the skin, so that a sufficient quantity of the metal ion is absorbed to increase vascularization locally. This method would most generally apply to wounds on the skin. Salves containing the transition metal can be applied topically to induce new blood vessel formation locally, thereby improving oxygenation of the area and hastening wound healing.

Transdermal patches for use in the invention are matrices infused with the metal ions in a biologically compatible carrier affixed to the skin of the patient so that the metal diffuses or is carried into the desired area. Matrices suitable for loading with transition metal ions are known to the art. They include water insoluble films, foams, or gels suitable for drug dispersal. One such film can be made by combining hyaluronic acid with a polyanionic modified polysaccharide, e.g., as described by U.S. Pat. No. 5,017,229, hereby incorporated by reference.

Slow release devices can be made with the transition metal ions or salts bound to a glycosaminoglycan matrix (as in Sparer et al., 1983) in such a way as to release the ions over an extended period of time as desired, hence a "slow release" formulation.

Dosage and release rate are selected to provide a concentration range of the metals in the treated tissue from 1 μM to 300 μM. Solubility and therefore release rate can be controlled by selecting the anion.

When determining systemic dosage, any synergistic interactions of the transition metal ions with endogenous events occurring in the injured tissue will be taken into account to avoid undesired effects in non-injured tissues. To the extent (if any) there is synergy between endogenous responses to moderate degrees of hypoxia and the transition metals of the invention, systemic administration can be used to generate a tissue specific response. In this manner, angiogenesis would be stimulated in the hypoxic areas where it is required and potentially harmful neovascularization (e.g., proliferative retinopathy) in already well-vascularized tissues can be controlled or avoided. This method would be most appropriate for internal areas of hypoxia, such as atherosclerosis of the coronary artery, peripheral vessels, or vessels supplying the brain. Indications include occlusion of vessels that have already precipitated tissue damage, such as a myocardial or cerebral infarct, or hypoxia of any internal tissue or organ. TIA and angina are some of the indications for the use of the invention.

Appropriate dosage is determined to affect the targeted tissues without substantial systemic effect. In this way, the desired or affected tissue may be targeted by the therapy for a significantly enhanced response compared to the effect on non-targeted tissues.

Another embodiment involves local internal application during surgery by using a solid or semi-solid biologically compatible and resorbable matrix, infused with the metal in a diffusible form to be placed exactly where desired. For example, the film disclosed in U.S. Pat. No. 5,017,229 described above may be used.

Methods to screen for ions and determine optimum concentrations of transition metals Appropriate transition metal ions can be determined by the VEGF expression assays such as the one described below, or by standard RNAase protection assays. These assays also may be used to optimize concentrations of ions.

In one expression assay, cardiac myocytes prepared according to a modified procedure of Ogawa et al. (1992, incorporated by reference) are used as follows: Hearts from 2–3 day old Sprague-Dawley rat pups are excised and minced into 0.3–0.5 mm pieces. The tissue is then digested overnight at 4° C. with 0.1% trypsin in Hanks buffered salt solution. The trypsin is neutralized and the tissue then incubated 4–5 times with collagenase (CLS II Worthington) at 129 units/ml. The collagenase treated cells are then washed twice with ice cold Hanks buffered saline and the cells preplated twice for one hour to allow attachment of non-myocyte cells. Cell viability is assessed by trypan blue exclusion and cells plated in DMEM (Delbeccos modified eagles medium) with 10% fetal bovine serum (FBS) at $10^6$ cells/ml on 10 cm Falcon dishes. The cells are re-fed the following day with DMEM with 10% FBS. To avoid serum stimulation of cells, the medium would be changed to DMEM with 0.2% FBS at the initiation of the assay.

In order to evaluate efficacy and toxicity of the various candidate metals, concentrations of the transition metal to be tested would be introduced into the medium (DMEM with 0.2% FBS) at concentrations ranging from $10^{-9}$M to 1M, or until the most effective and least toxic range was established for each metal tested.

Optimal concentration range would be determined as that range wherein VEGF mRNA was maximally stimulated after 4–8 hrs of exposure to the transition metal-containing medium. Gene expression will be assessed using standard methods (e.g., Northern blotting, hybridization with a homologous probe and a radionuclide detection system).

Toxicity would be established according to standard animal models well known to those in the art for determination of metal ion toxicity.

The following example of an expression assay is not intended to be limiting.

EXAMPLE 1

Hep3B cells were obtained through American Type Culture Collection. A C6 rat glioma cell line can be obtained from the American Type Culture Collection, Rockville, Md., under accession number ATCC #CCL107. Both cell types were cultured in MEM Alpha medium (JRH Biosciences, Lenexa, Kans.) supplemented with penicillin (100 units/ml), streptomycin (100 μg/ml) and 10% defined/supplemented bovine calf serum (Hyclone, Logan, Utah) and were maintained in a humidified 5% $CO_2$ incubator at 37° C. All experiments were begun when the cells approached confluence. In experiments with cobalt chloride, 10 mM $CoCl_2$ was added to complete media (media plus 10% serum) to a final concentration of 100 μM $CoCl_2$. An identical volume of complete media without $CoCl_2$ was added to control cells.

Figure 2A:
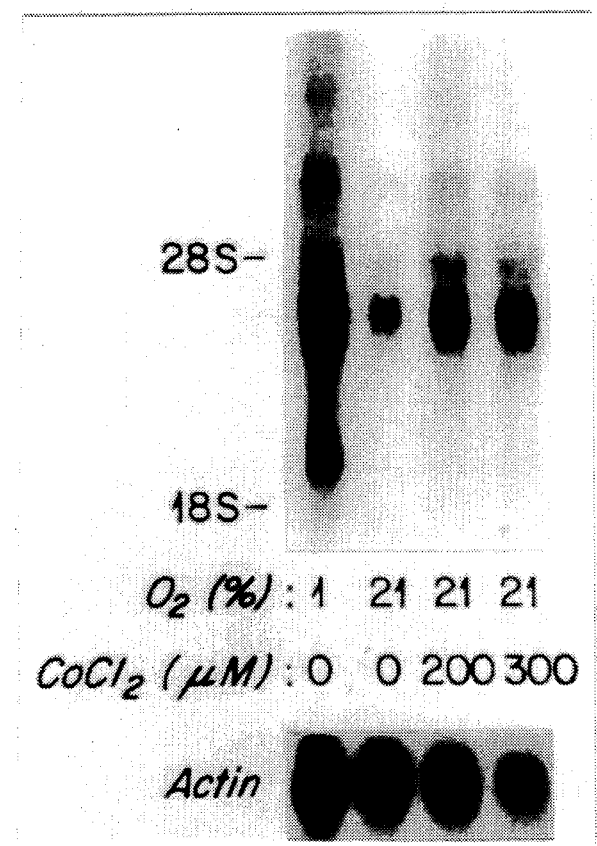
FIGS. 2a and 2b show Northern blot analysis of cobalt dose-response of VEGF induction in C6 glioma cells (a) and in primary rat cardiac myocyte cultures (b). All mRNA was harvested at 24 hrs. Concentrations of $CoCl_2$ in the medium are shown for each lane. β-actin mRNA controls are depicted at the bottom of the figure.
Figure 2B:
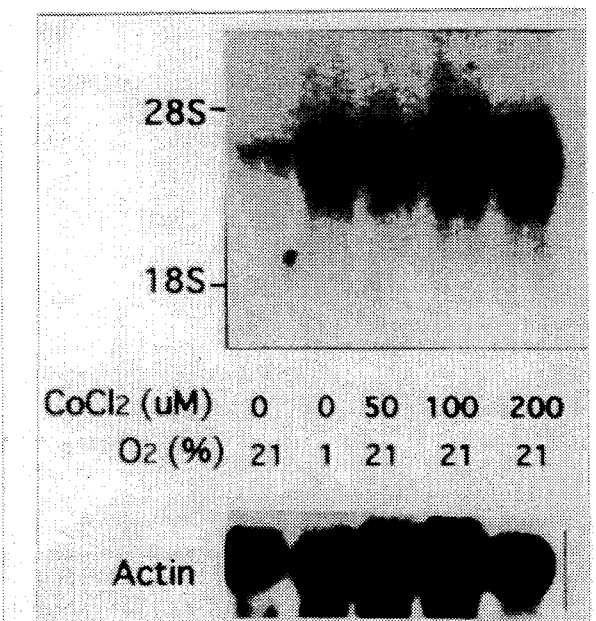

Using these cell types and this method (and methods for cardiac myocytes), the inventors have determined that 50–300 μM $CoCl_2$ strongly induces VEGF gene expression in different cell lines (FIGS. 1 and 2). They have further determined that the gene products c-fos and c-jun are also upregulated by this treatment.

III. Medical indications for the invention

The patient population that would benefit from this therapy is large and includes any patients requiring angiogenesis or recovery from endothelial cell damage or loss. Examples would be patients with atherosclerosis, those with diabetic pathology including chronic skin lesions, any patient with bone fractures or wounds that do not heal readily, patients recovering from surgeries that require rapid revascularization of affected areas or where endothelium is damaged (e.g., vascular graft surgery, balloon angioplasty), or those with conditions such as frostbite, gangrene, or poor circulation. Patients presenting with transient ishcemic attacks (TIA) or angina are candidates for treatment according to the invention.

What is claimed is:

1. A method of increasing vascularization of tissue in a patient in need thereof by administering a composition comprising a transition metal ion capable of stimulating vascularization in an amount suitable to stimulate said vascularization.

2. The method of claim 1, wherein the composition is administered locally to the hypoxic tissue.

3. The method of claim 2 wherein the composition is administered topically as a salve or patch.

4. The method of claim 2 wherein the composition is administered from a controlled, slow-release matrix.

5. The method of claim 1 wherein the composition is systemically administered at a concentration that is non-toxic and ineffective to increase vascularization in non-hypoxic tissue.

6. The method of claim 1, wherein the transition metal ion is capable of inducing expression of the vascular endothelial growth factor (VEGF) gene.

7. The method of claim 1, wherein the transition metal ion is chosen from the group consisting manganese and cobalt.

8. The method of claim 1 wherein the composition contains more than one transition metal ion.

9. The method of claim 1 wherein the tissue vascularized is cardiac tissue.

10. The method of claim 1 wherein the tissue vascularized is a diabetic ulcer.

11. The method of claim 1 wherein the tissue vascularized is a surgical wound.

12. The method of claim 1 wherein the tissue vascularized is neuronal tissue damaged incident to ischemia of the brain.

13. The method of claim 1 wherein the tissue vascularized is damaged as a result of peripheral vascular disease.

14. A composition of matter suitable for local administration to a human patient, the composition of matter comprising a transition metal ion in a sterile, biologically compatible carrier provided as a salve, gel, film, or patch at a dosage effective to increase vascularization in hypoxic tissue.

15. The composition of claim 14, wherein the transition metal ion is capable of inducing expression of the vascular endothelial growth factor (VEGF) gene.

16. The composition of claim 14, wherein the transition metal ion is selected from the group consisting of manganese and cobalt.

17. The composition of claim 14 wherein the composition contains more than one transition metal ion.

18. The composition of claim 14 wherein the transition metal ion is present in a concentration to provide a concentration of between 1 μM and 3001 μM to treated tissue.

19. A composition comprising transition metal ions selected from the group consisting of manganese and cobalt, formulated in a slow-releasing matrix suitable for local application to release the transition metal ions continually over a prolonged period in an amount effective to increase vascularization locally.

20. The composition of claim 19, wherein the transition metal ion is capable of inducing expression of the vascular endothelial growth factor (VEGF) gene.

21. The composition of claim 19, wherein the composition contains more than one transition metal ion.

22. The composition of claim 19 wherein the composition is suitable for topical application.

23. The composition of claim 19 wherein the composition is a salve, a gel, or a patch.

24. The composition of claim 19 wherein the composition is a controlled slow release matrix.

25. The composition of claim 19 wherein the composition is formulated to release the transition metal ion at a rate of between 1 μg and 10 mg/hour.

26. The composition of claim 24 or claim 25 wherein the composition is formulated to release the transition metal ion substantially continuously for a period of at least one day.

* * * * *

UNITED STATES PATENT AND TRADEMARK OFFICE
CERTIFICATE OF CORRECTION

PATENT NO. : 5,480,975

DATED : January 2, 1996

INVENTOR(S) : Goldberg et al.

It is certified that error appears in the above-identified patent and that said Letters Patent is hereby corrected as shown below:

On the Title page item [56] References cited, insert the following :

U.S. 4,851,403 - Picker et al.; U.S. 5,073,492 - Chen et al.; U.S. 5,194,596 - Tischer et al.; U.S. 5,219,739 - Tischer et al.; EP 0496641A2 - Europe; Beru, N., et al., "Expression of the Erythropoietin Gene", 1986, Molec. and Cell. Biol., Vol. 6, pp. 2571-75; Bondurant, M.C., et al., "Anemia Induces Accumulation of Erythropoietin mRNA in the Kidney and Liver", 1986, Molec. and Cell. Biol., Vol. 6, pp. 2731-33; Criscuolo, G.R., et al., "Cytosolic Calcium Changes in Endothelial Cells Induced by a Protein Product of Human Gliomas Containing Vascular Permeability Factor Activity", 1989, J. Neurosurg, Vol. 71, pp. 884-91; Goldberg, M.A., et al., "Regulation of the Erythropoietin Gene: Evidence that the Oxygen Sensor is a Heme Protein", 1988, Science, Vol. 242, pp. 1412-15; Kourembanas, S., et al., "Oxygen Tension Regulates the Expression of the Platelet-derived Growth Factor-B Chain Gene in Human Endothelial Cells", 1990, J. Clin. Invest., Vol. 86, pp. 670-74; Kourembanas, S., et al., "Hypoxia Induces Endothelin Gene Expression and Secretion in Cultured Human Endothelium", 1991, J. Clin. Invest., Vol. 88, pp.1054-57; Leung, D.W., et al., "Vascular Endothelial Growth Factor Is a Secreted Angiogenic Mitogen", 1989, Science, Vol. 246, pp. 1306-09; Longo, L.D., et al., "Acute Hypoxia Increases Ornithine Decarboxylase Activity and Polyamine Concentrations in Fetal Rat Brain", 1993, Proc. Natl. Acad. Sci. USA, Vol. 90, pp. 692-696;

UNITED STATES PATENT AND TRADEMARK OFFICE
CERTIFICATE OF CORRECTION

PATENT NO. : 5,480,975

DATED : January 2, 1996

INVENTOR(S) : Goldberg et al.

Plate, K.H., et al., "Vascular Endothelial Growth Factor is a Potential Tumour Angiogenesis Factor in Human Gliomas In Vivo", 1992, Nature, Vol. 359, pp. 845-48; Shreeniwas, R., et al., "Hypoxia-Mediated Induction of Endothelial Cell Interleukin-1α: An Autocrine Mechanism Promoting Expression of Leukocyte Adhesion Molecules on the Vessel Surface", 1992, J. Clin. Invest., Vol. 90, pp. 2333-39; Shweiki, D., et al., "Vascular Endothelial Growth Factor Induced by Hypoxia May Mediate Hypoxia-Initiated Angiogenesis", 1992, Nature, Vol. 359, pp. 843-45; Sparer, R.V., et al., "Controlled Release From Glycosaminoglycan Drug Complexes", 1983, Controlled Release Delivery Systems; by Marcel Dekker, Inc., Chapter 6, pp. 107-19; Tischer, E., et al., "The Human Gene for Vascular Endothelial Growth Factor: Multiple Protein Forms are Encoded Through Alternative Exon Splicing", 1991, J. Biol. Chem., Vol. 266, pp. 11947-54;

Col. 1, line 39, "B" should be --$\beta$--.

Col. 2, line 16, delete "affected".

Col. 5, claim 1, line 59, after "administering" insert --thereto--.

Col. 6, claim 24, line 58, after "controlled" insert a comma.

UNITED STATES PATENT AND TRADEMARK OFFICE
CERTIFICATE OF CORRECTION

PATENT NO. : 5,480,975
DATED : January 2, 1996
INVENTOR(S) : Goldberg, et al

It is certified that error appears in the above-indentified patent and that said Letters Patent is hereby corrected as shown below:

Column 6, claim 25, line 59, "19" should be --24--.

Signed and Sealed this

Twentieth Day of August, 1996

Attest:

BRUCE LEHMAN

Attesting Officer  Commissioner of Patents and Trademarks